(12) United States Patent
Pfleiderer et al.

(10) Patent No.: US 6,750,335 B2
(45) Date of Patent: *Jun. 15, 2004

(54) NUCLEOSIDE DERIVATIVES WITH PHOTOLABILE PROTECTIVE GROUPS

(75) Inventors: Wolfgang Pfleiderer, Constance (DE); Sigrid Bühler, Constance (DE); Heiner Giegrich, Waldkraiburg (DE)

(73) Assignee: Nigu Chemie GmbH, Waldkraiburg (DE)

( * ) Notice: Subject to any disclaimer, the term of this patent is extended or adjusted under 35 U.S.C. 154(b) by 70 days.

This patent is subject to a terminal disclaimer.

(21) Appl. No.: 10/108,565

(22) Filed: Mar. 29, 2002

(65) Prior Publication Data

US 2002/0146737 A1 Oct. 10, 2002

Related U.S. Application Data

(63) Continuation of application No. PCT/EP00/09958, filed on Oct. 10, 2000.

(30) Foreign Application Priority Data

Oct. 29, 1999 (DE) .......................... 199 52 113

(51) Int. Cl.$^7$ ................................ C07H 1/02

(52) U.S. Cl. ................. 536/55.3; 536/25.3; 536/26.1

(58) Field of Search ................ 536/55.3, 25.3, 536/26.1

(56) References Cited

U.S. PATENT DOCUMENTS

| | | | |
|---|---|---|---|
| 5,623,068 A | 4/1997 | Reddy et al. | |
| 5,635,608 A | 6/1997 | Haugland et al. | |
| 5,763,599 A | 6/1998 | Pfleiderer et al. | |
| 5,843,655 A | 12/1998 | McGall | |
| 6,153,744 A | 11/2000 | Pfleiderer et al. | |

FOREIGN PATENT DOCUMENTS

| | | |
|---|---|---|
| DE | 36 06 394 | 9/1987 |
| DE | 36 06 395 | 9/1987 |
| WO | WO 94/10128 | 5/1994 |
| WO | WO 96/18634 | 6/1996 |
| WO | WO 97/44345 | 11/1997 |
| WO | WO 98/39348 | 9/1998 |

OTHER PUBLICATIONS

Bühler, S., et al., "New Photolabile Protecting Groups of the 2–(2–Nitrophenyl) Ethoxycarbonyl– and the 2–(2–Nitrophenyl) Ethylsulfonyl–type for the Oligonucleotide synthesis". Nucleosides & Nucleotides, 18 (6&7), 1281–1283 (1999).

Giegrich, H., et al., "New Photolabile Protecting Groups in Nucleoside and Nucleotide Chemistry—Synthesis, Cleavage Mechanisms and Applications". Nucleosides & Nucleotides, 17 (9–11), 1987–1996 (1998).

Korri–Youssoufi, H., et al., "Toward Bioelectronics: Specific DNA Recognition Based on an Oligonucleotide–Functionalized Polypyrrole". J. Am. Chem. Soc. (119) 7388–7389 (1997).

McGall, Glenn H., et al., "The Efficiency of Light Directed Synthesis of DNA Arrays on Glass Substances". J. Am. Chem. Soc. (119) 5081–5090 (1997).

Pirrung, Michael C., et al., "Comparison of methods for Photochemical Phosphoramidite–Based DNA Synthesis". J. Org. Chem. (60) 6270–6276 (1995).

Hasan, Ahmad, et al., "Photolabile Protecting Groups for Nucleosides: Synthesis and Photodeprotection Rates". Tetrahedron (53) 4247–4264 (1997).

Buhler, S., et al., "New photolabile protecting groups of the 2–(2–nitrophenyl) ethoxycarbonyl– and the 2–(2–nitrophenyl) ethyl–sulfonyl–type for the oligonucleotide synthesis". Chemical Absract, 33–Carbohydrates, 131:243502, vol. 131, No. 18 (1999).

*Primary Examiner*—James O. Wilson
*Assistant Examiner*—Patrick Lewis
(74) *Attorney, Agent, or Firm*—Nath & Associates PLLC; Gary M. Nath; Jerald L. Meyer

(57) ABSTRACT

The invention relates to nucleoside derivatives with photolabile protecting groups of general formula (I)

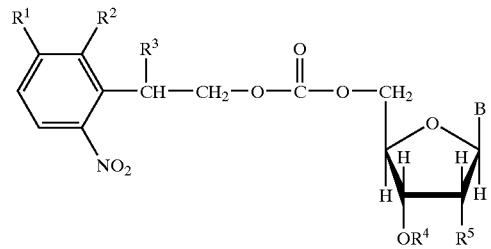

wherein $R^1$ is H, F, Cl, Br, I, or $NO_2$; $R^2$ is H or CN, provided that $R^1$ and $R^2$ are not simultaneously H; $R^3$ is H, 1–4 C alkyl, or phenyl; $R^4$ is H or a conventional functional group for the synthesis of oligonuleotides; $R^5$ is H, OH, halogen or $XR^6$, where X=O or S, and $R^6$ is a conventional nucleotide protecting group; and B is adenine, cytosine, guanine, thymine, uracil, 2,6-diaminopurin-9-yl, hypoxanthin-9-yl, 5-methylcytosin-1-yl, 5-amino-4-imidazolcarboxamid-1-yl or 5-amino-4-imidazolcarboxamid-3-yl, where, if B is adenine, cytosine or guanine the primary amine functionality, optionally, carries a permanent protecting group. Furthermore, these derivatives may be used for the light-controlled synthesis of oligonucleotides on a DNA chip.

13 Claims, No Drawings

OTHER PUBLICATIONS

Giegrich, H., et al., "New photolabile protecting groups in nucleoside and nucleotide chemistry—synthesis, cleavage mechanisms and applications". Chemical Abstracts, 33–Carbohydrates, 129:343670, vol. 129, No. 26 (1998).

Pfleiderer, W., et al., "New protecting groups in nucleoside and nucleotide chemistry". Chemical Abstracts, 108:38280, vol. 108, (1988).

Pfleiderer, W., et al., "New Protecting Groups in Nucleoside and Nucleotide Chemistry". *Biophosphates and Their Analogues—Synthesis, Structure, Metabolism and Activity*, Brusik, K.S. and Strec, W.J. (eds.), Proceedings and the $2^{nd}$ International Symposium on Phosphorus Chemistry Directed Towards Biology, Lodz, Poland, Sep. 8–12, 1986, pp. 133–142.

NUCLEOSIDE DERIVATIVES WITH PHOTOLABILE PROTECTIVE GROUPS

This application is a continuation application of International application No. PCT/EP00/09958, with an International Filing Date of Oct. 10, 2000, the entire contents of which are hereby incorporated by reference in its entirety.

TECHNICAL FIELD

The subject matter of the present invention are nucleoside derivatives with photolabile protective groups, processes for preparing the same and the use thereof.

Prior art

Photolabile protective groups for the hydroxy and phosphate functions in nucleosides or nucleotides, respectively, are of particular interest because, for example, they are suitable for light-controlled parallel syntheses of oligonucleotides on a solid carrier (cf. S. P. A. Fodor et al., Science 1991, 251, page 767 et seq.). With their aid, it is possible to produce so-called DNA chips (i.e. carrier platelets on the surface of which many different oligonucleotides are arranged) which, in turn, are required in molecular biology, for example for sequence analyses or expression studies.

According to the prior art, especially the o-nitrobenzyl group and its derivatives have been used as photolabile protective groups in nucleoside and nucleotide chemistry, respectively (cf. V. N. R. Pillai, Org. Photochem. 1987, 9, page 225 et seq., and J. W. Walker et al., J. Am. Chem. Soc. 1988, 110, pages 7170 et seq.) In addition, protective groups of the pyrenyl methoxy carbonyl type have been used (cf. WO 98/39 348). The slow and, in part, incomplete deprotection of the relevant nucleoside or nucleotide derivatives has turned out to be a particular disadvantage of these protective groups. In addition, some undesirable byproducts in the form of toxic nitrosophenyl compounds may result when the o-nitrobenzyl compounds are separated.

The 2-(2-nitrophenyl)ethoxy carbonyl group and the 2-(2-nitrophenyl)ethyl sulfonyl groups and their derivatives have been introduced as additional photolabile protective groups for nucleic acid chemistry (cf. WO 96/18 634 and WO 97/44 345) which may be separated more rapidly and completely when compared to the above-mentioned nitrobenzyl or pyrenyl methoxy carbonyl groups.

One disadvantage of these protective groups turned out to be the deprotection of the relevant nucleosides or nucleotides which is still comparatively slow and incomplete.

SUMMARY OF THE INVENTION

Therefore, it was the objective of the present invention to develop nucleoside derivatives with photolabile protective groups for the 5'-OH function in the sugar portion which does not have the above-mentioned disadvantages of the prior art, but may be deprotected comparatively rapidly, quantitatively and without formation of undesirable byproducts.

This invention achieves this objective by nucleoside derivatives of the general formula (I) according to claim 1, because it has surprisingly been shown that the protective groups of the invention may be separated much more rapidly and completely than, for example, the o-nitrobenzyl groups. In addition, no major amounts of byproducts have found upon deprotection so far, which was not foreseeable either.

The nucleoside derivatives of the invention have the following general formula (I)

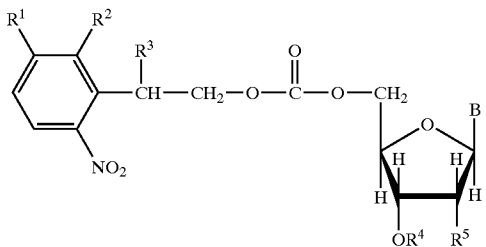

wherein the radicals $R^1$ and $R^2$ on the phenyl ring may be defined as follows:
$R^1$=H, F, Cl, Br, I, $NO_2$
$R^2$=H, CN,
$R^1$ and $R^2$ not being H at the same time The radical $R^3$ which is located on the $C_2$ atom of the o-nitrophenyl ethyl group may either be H, an alkyl radical comprising 1 bis 4 carbon atoms or a phenyl radical. Said alkyl radical may be linear or branched.

The nucleoside portion of the compounds of the invention consists of the customary D-ribofuranose and 2'-deoxyribofuranose units and the pyrimidine (B=cytosine, thymine, uracil) or purine bases (B=adenine, guanine). 2,6-diaminopurine-9-yl, hypoxanthine-9-yl, 5-methylcytosine-1-yl, 5-amino-4-imidazol carboxylic acid amide-1-yl or 5-amino-4-imidazol carboxylic acid amide-3-yl radicals may also be used as bases.

The OH group(s) in the ribofuranoside or 2'-deoxyribofuranose portion may be free or protected as required. In order to protect the 3' position ($R^4$ position), the following known phosphite amide groups have turned out to be effective, for example

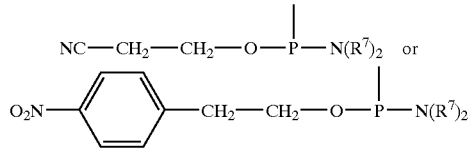

wherein the $R^7$ groups may be the same or different and represent linear or branched alkyl radicals having 1 to 4 carbon atoms. Preferably they are ethyl or isopropyl radicals.

In position 2' of the ribofuranoside portion (position $R^5$), a free or protected OH group may be present in addition to the hydrogen or halogen atom (especially F, Cl, Br). In that case, any protective group customary in nucleotide chemistry ($R^6$) may be used. In particular, use may be made of the customary alkyl, alkenyl, acetal or silyl ether protective groups for oxygen atoms (X=O). $R^5$ may also be an S-alkyl group (X=S, $R^6$=alkyl). O-methyl or O-ethyl radicals are preferred examples for O-alkyl protective groups, O-allyl radicals for O-alkenyl protective groups, O-tetrahyropyranyl or O-methoxytetrahydropyranyl radicals for O-acetal protective groups and O-t-butyldimethylsilyl radicals for O-silylether protective groups.

In accordance with a preferred embodiment, the pyrimidine or purine bases having primary amino functions (e.g. adenine, cytosine and guanine) may also have permanent protective groups, preferably on a carbonyl basis. For this purpose, especially phenoxy acetyl or dimethyl formamidino radicals are preferred, because they may be used for all of the three cited bases. In addition, there are special protective groups which are introduced only with certain bases. In case of adenine, for example, these are benzoyl or p-nitrophenyl ethoxy carbonyl (p-NPEOC) radicals. In addition to the p-NPEOC radicals, isobutyroyl or p-nitrophenyl ethyl (p-NPE) protective groups may be introduced for guanine (for the O-6 function). Finally, benzoyl or isobutyroyl are suitable protective groups for cytosine in addition to p-NPEOC radicals.

Preparation of the nucleoside derivatives is carried out in at least two stages. In the first stage, an alcohol of the general formula (II)

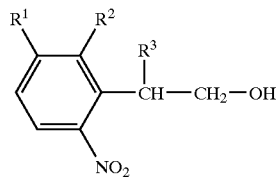

wherein $R^1$, $R^2$ and $R^3$ are as defined above is reacted with a phosgene derivative, preferably in a non-plar organic solvent at temperatures between −20 and +25° C. In addition to phosgene, diphosgene (chloroformic acid trichloromethyl ester) or triphosgene (bistrichloromethyl carbonate) may be used as the phosgene derivative.

The alcohol component is known in most cases or may be prepared analogously by known methods. In stage (a), toluene or THF is preferably used as the non-polar organic solvent. Even though the reaction components may be used in an almost stoichiometric ratio, the phosgene derivative is preferably used in a clear excess based on the alcohol component. The concentration of the alcohol component may also be varied within wide limits, but it has turned out to be particularly advantageous to adjust this concentration to 0. 1 to 10.0 mmol per 10 ml of solvent.

This reaction (duration of the reaction about 1 to 2 hours), yields 95% or more of the relevant chlorocarbonic acid esters of the general formula (IV) which are of high purity:

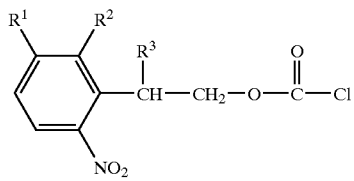

The pertinent products are preferably worked up by first distilling off any excess phosgene derivative and the solvent under vacuum. In stage (b), the chlorocarbonic acid ester (IV) may then be reacted without further work-up with the nucleosides of the general formula (III)

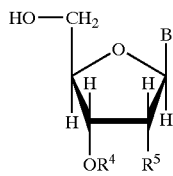

wherein $R^4$, $R^5$ and B are as defined above.

The reaction is preferably carried out in a solvent mixture consisting of dichloromethane and a polar organic solvent, optionally in the presence of a base, at temperatures between −60 and +25° C. DMF or pyridine is preferably used as the polar organic solvent, no additional base being required when pyridine is used. However, if a solvent mixture of dichloromethane/DMF is used, it is recommended to add a base such as pyridine, triethyl amine or ethyl diisopropyl amine in order to scavenge the protons released during the reaction. The mixing ratio of dichloromethane to pyridine or DMF is not critical, but it is preferred to use 1 to 3 parts by vol. of dichloromethane per part by vol. of pyridine or DMF, respectively.

In a preferred embodiment, the relevant nucleoside (III) which was dissolved in pyridine or DMF/base is fed into the reaction vessel and a solution of the chlorocarbonic acid ester in dichloromethane added dropwise at the pertinent reaction temperature. The mol ratio of nucleoside to chlorocarbonic acid ester may be adjusted to about 1:1 in accordance with stoichiometry. Preferably, an excess of chlorocarbonic ester is added in such an amount that the mol ratio of nucleoside to chlorocarbonic acid ester is 1:1 to 1:2. Finally, the concentration of the nucleoside in the solvent mixture may be varied within wide limits, but is preferably adjusted to 0.1 to 3.0 mmol per 10 ml of solvent.

After completion of the reaction (reaction time about 5 to 6 hours), the nucleoside derivatives of the invention may be isolated and purified by known methods, for example by dilution with dichloromethane, washing out all salts with water, drying of the organic phase, concentration of the solution or crystallisation followed by silica gel chromatography. That way, it is possible to obtain the relevant nucleoside derivatives in high purity and good yields (about 70 to 80%).

According to a preferred embodiment of the invention, it is possible to introduce the phosphite amide group

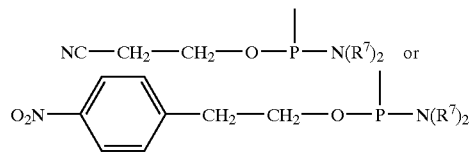

into position 3' of the nucleoside derivatives with $R^4$=H by known methods after reaction stage (b). In general, this reaction with the pertinent phosphines is carried out in the presence of 1H tetrazol as activator in a solvent mixture consisting of dichloromethane and acetonitrile at temperatures between 0 and 25° C. Preferably the phosphine is used in a 1.5 to 3-fold molar excess, while the mol ratio of phosphine to 1H tetrazol is adjusted to 2 to 4: about 1.0. The quantity ratio of dichloromethane to acetonitril is comparatively uncritical and is preferably 1:1 to 4:1. After completion of the reaction, the nucleoside may be worked up as described in stage (b).

As irradiation experiments with polychromatic light with wavelenghts of >289 nm have shown, the nucleosides of the invention may be deprotected very quickly ($t_{0.5}$=20 to 50 sec.) and to a considerable extent (yields of up to 97%) so that the special requirements of photolability of the protective groups are met in an excellent manner.

Owing to these special characteristics, the nucleosides of the invention are excellently suited for preparing oligonucleotides through the light-controlled separation of protective groups, especially on solid carrier plates.

The following examples will explain the invention in greater detail.

EXAMPLES

A) Synthesis of the Alcohol Precursors

Example A.1
3-acetylamino-1-ethylbenzene (1) [I]

[I] H. Wieland und L. Horner, Liebigs Ann., 536, 89 (1938)

With cooling in an ice bath, 27 g (25 ml, 0.22 mol) of 3-ethyl aniline are added to 100 ml of acetic acid anhydride. After 10 minutes in the ice bath, the mixture is stirred at room temperature for a further 20 minutes and then concentrated as far as possible by means of a rotary evaporator. The raw product (36.6 g) is purified by distillation under high vacuum. 32.1 g (0.2 mol, 89%) of (1) are obtained as a slightly yellowish solid having a boiling point of 110 to 114° C. (0.05 mbar).

Physical data of (1):

M.P.: 30–32° C. (Lit [I]: 33–34° C.).

DC (silica gel, PE/EE 1:1): $R_f$=0.42.

$^1$H-NMR (250 MHz, CDCl$_3$): 7.60 (s(br), 1H, NH), 7.34–7.16 (m, 3H, arom. H), 6.92 (d, 1H, arom. H), 2.59 (q, 2H, CH$_2$), 2.14 (s, 3H, COCH$_3$), 1.18 (t, 3H, CH$_3$).

UV spectrum (MeOH). $\lambda_{max}$ [nm] (log $\epsilon$): 206 (3.41), 242 (3.10), [280 (1.76)].

Example A.2
5-amino-1-ethyl-2-nitrobenzene [I] (2), 3-amino-1-ethyl-2,4-dinitrobenzene (3), 3-amino-1-ethyl-2,6-dinitrobenzene (4) and 5-amino-1-ethyl-2,4-dinitrobenzene (5)

[I] H. Wieland und L. Horner, Liebigs Ann., 536, 89 (1938)

For this reaction, a KPG stirrer is recommended 15 g (92 mmol) of 3-acetylamino-1-ethyl benzene (1) are added to 70 ml of concentrated sulfuric acid cooled to −20° C. in such a manner that the temperature remains below 0° C. Then 9.5 g (6.2 ml, 0.15 mmol) of fuming nitric acid are added dropwise over 30 min. in such a manner that the temperature does not rise above −3° C. After one hour of stirring in the ice bath, the reaction mixture is poured onto ice, neutralised with solid sodium carbonate and extracted once with 400 ml and twice with 200 ml each of Et$_2$O. After drying over Na$_2$SO$_4$ and rotation, the brown oil obtained is heated to boiling point for two hours with 100 ml of conc. HCl. After cooling, the separated precipitate is removed by suction, slurried in 1 n NaOH and extracted three times with 100 ml each of Et$_2$O. The organic phase is dried over Na$_2$SO$_4$ and then concentrated by means of a rotary evaporator. The raw product is applied to silica gel and pre-purified by flash chromatography (127 g of silica gel, 6×13 cm, LM:PE/EE, cond. 8:1, gradient of 8:1 to 4:1). 110 mg of (3) (0.5 mmol, 0.6%), 790 mg of (4) (4 mmol, 4%) and 7 g of a mixture of (1) and (5) is obtained. This mixture may be separated by boiling in 15 ml of HCl/75 ml of H$_2$O. The desired product remains in solution as hydrochloride, while the dinitro derivative remains as a solid (or oil). The liquid is decanted, neutralised with sodium carbonate, extracted three times with 50 ml each of Et$_2$O, dried over Na$_2$SO$_4$ and rotated. 4.3 g (26 mmol, 28%) of (2) are obtained as a yellow solid. Taking up the residue in Et$_2$O, drying over Na$_2$SO$_4$ and rotation yields 2.34 g (11 mmol, 12%) of (5) as a brown solid.

Physical data of (2):

M.P.: 84–85° C. (Lit [I]: 80–81° C.).

DC (silica gel, PE/EE 7:3): $R_f$=0.27.

$^1$H-NMR (250 MHz, CDCl$_3$): 7.96 (m, 1H, H(6)), 6.47 (m, 2H, H(3), H(5)), 4.23 (s(br), 2H, NH$_2$), 2.93 (q, 2H, CH$_2$), 1.24 (t, 3H, CH$_3$).

$^{13}$C-NMR (600 MHz, CDCl$_3$): 151.30 (C(5)), 143.25 (C(1)), 139.42(C(2)), 128.35(C(3)), 115.35 (C(6)), 111.72 (C(4)), 27.48 (CH$_2$), 14.67 (CH$_3$).

UV spectrum (MeOH), $\lambda_{max}$ [nm] (log $\epsilon$): 203 (4.21), 231 (3.82), [245 (3.69)], [372 (4.09)].

MS (EI 70 eV, m/z (%)): M$^+$ 166 (55), 149 (100), 121 (42), 93 (26), 65 (35), 52 (23), 39 (32).

Physical data of (3):

M.P.: 85–89° C.

DC (silica gel, PE/EE 7:3): $R_f$=0.77.

$^1$H-NMR (600 MHz, CDCl$_3$): 8.24 (d, 1H, H(5)), 7.02 (s(br), 2H, NH$_2$), 6.66 (d, 1H, H(6)), 2.70 (q, 2H, CH$_2$), 1.26 (t, 3H, CH$_3$).

$^{13}$C-NMR (600 MHz, CDCl$_3$): 147.46 (C(1)), 139.02 (C(2)), 138.80 (C(3)), 132.23 (C(4)), 129.40 (C(5)), 116.86 (C(6)), 26.57 (CH$_2$), 14.42 (CH$_3$).

UV spectrum (MeOH), $\lambda_{max}$ [nm] (log $\epsilon$): 202 (4.08), 225 (4.27), 270 (3.78), 399 (3.72).

Physical data of (4):

M.P.: 103–106° C.

DC (silica gel, PE/EE 7:3): $R_f$=0.43.

$^1$H-NMR (600 MHz, CDCl$_3$): 7.95 (d, 1H, H(5)), 6.70 (d, 1H, H(4)), 4.96 (s(br), 2H, NH$_2$), 2.92 (q, 2H, CH$_2$), 1.31 (t, 3H, CH$_3$).

$^{13}$C-NMR (600 MHz, CDCl$_3$): 143.94 (C(3)), 139.83 (C(6)), 137.48 (C(2)), 136.16 (C(1)), 129.32 (C(5)), 114.67 (C(4)), 22.29 (CH$_2$), 14.62 (CH$_3$).

UV spectrum (MeOH), $\lambda_{max}$ [nm] (log $\epsilon$): 202 (4.19), 225 (3.93), 346 (3.94).

Physical data of (5):

M.P.: 96–101° C.

DC (silica gel, PE/EE 7:3): $R_f$=0.27.

$^1$H-NMR (250 MHz, CDCl$_3$): 8.98 (s, 1H), 6.69 (s, 1H), 6.51 (s(br), 2H, NH$_2$), 2.98 (q, 2H, CH$_2$), 1.26 (t, 3H, CH$_3$).

$^{13}$C-NMR (600 MHz, CDCl$_3$): 147.97 (C(1)), 146.95 (C(5)), 138.16 (C(2)), 129.03 (C(4)), 125.70 (C(3)), 119.59 (C(6)), 27.13 (CH$_2$), 14.19 (CH$_3$).

UV spectrum (MeOH), $\lambda_{max}$ [nm] (log $\epsilon$): 202 (4.15), [228 (4.01)], 265 (3.99), 342 (4.02), [361 (4.00)].

MS (EI 70 eV, m/z (%)) M$^+$ 211 (56), 194 (100), 148 (26), 118 (30), 91 (30), 65 (24), 52 (38), 39 (31).

Example A.3
5-chloro-1-ethyl-2-nitrobenzene (6)

1.66 g (10 mmol) of 5-amino-1-ethyl-2-nitrobenzene (2) are dissolved in a 60° C. mixture of 5 ml of conc. HCl and 25 ml H$_2$O and cooled rapidly in an ice bath. At a temperature below 5° C., diazotisation is carried out with 760 mg (11 mmol) of sodium nitrite in 10 ml of H$_2$O. After 10 minutes, a pinch of urea from a spatula is added and the mixture stirred for another 5 minutes in the ice bath. This reaction mixture is poured into an 80° C. solution of 1.5 g of copper(I) chloride in 10 ml of conc. HCl and 5 ml H$_2$O which results in considerable evolvement of gas. The solution is held at this temperature for another 30 min. After cooling, the reaction solution is extracted three times with 50 ml each of EE and the combined organic phases washed with 50 ml each of NaOH and H$_2$O. After drying over Na$_2$SO$_4$, concentration by means of a rotary evaporator is carried out. The crude product is placed on silica gel and purified by flash chromatography (40 g of silica gel, 3.5×13 cm, LM: PE). 863 mg (4.6 mmol, 46%) of (6) are obtained as a yellow oil.

Physical data of (6):

DC (silica gel, PE/EE 4:1): $R_f$=0.77.

$^1$H-NMR (250 MHz, CDCl$_3$): 7.85 (d, 1H, H(3)), 7.34 (d, 1H, H(6)), 7.29 (dd, 1H, H(4)), 2.90 (q, 2H, CH$_2$), 1.27 (t, 3H, CH$_3$).

UV spectrum (MeOH), $\lambda_{max}$ [nm] (log $\epsilon$): 206 (4.09), [216 (3.91)], 263 (3.79), [334 (2.84)].

$C_8H_8ClNO_2$ (185.61 g/mol): Calc.: C, 51.77, H, 4.34, N, 7.55; found: C, 51.65, H, 4.34, N, 7.63.

Example A.4

5-bromo-1-ethyl-2-nitrobenzene (7)

1.66 g (10 mmol) of 5-amino-1-ethyl-2-nitrobenzene (2) are added to a mixture of 12.5 ml of 48% hydrobromic acid and 7.5 ml of $H_2O$ heated to 60° C. and cooled rapidly in an ice bath. At a temperature below 5° C., the mixture is subjected to diazotisation with 760 mg (11 mmol) of sodium nitrite in 10 ml of $H_2O$. After 10 minutes, a pinch of urea from a spatula is added and the mixture stirred for another 5 minutes in the ice bath. This reaction mixture is fed into a suspension of 1.5 g (6 mmol) of copper sulfate pentahydrate and 600 mg (9.4 mmol) of copper powder in 12.5 ml of 48% hydrobromic acid and 7.5 ml of $H_2O$ and heated to 80° C. for 30 min. After cooling, the reaction solution is extracted 3 times with 50 ml each of EE and the combined organic phases washed once with 50 ml each of 1 n NaOH and $H_2O$. After drying over $Na_2SO_4$, concentration by means of a rotary evaporator is carried out. The crude product is placed on silica gel and purified by flash chromatography (40 g of silica gel, 3.5×13 cm, LM: PE/EE, cond. PE, gradient: 150 ml PE, 600 ml 150: 1, 150 ml 150:2). 1.55 g (6.7 mmol, 67%) of (7) are obtained as a yellow oil.

Physical data of (7):

DC (silica gel, PE/EE 4:1): $R_f$=0.76.

$^1$H-NMR (250 MHz, $CDCl_3$): 7.76 (d, 1H, H(3)), 7.50 (d, 1H, H(6)), 7.45 (dd, 1H, H(4)), 2.89 (q, 2H, $CH_2$), 1.27 (t, 3H, $CH_3$).

UV spectrum (MeOH), $\lambda_{max}$ [nm] (log ε): 203 (4.19), [217 (3.98)], 267 (3.91), [320 (3.21)].

$C_8H_8BrNO_2$ (230.07 g/mol): Calc.: C, 41.77, H, 3.50, N, 6.09; found.: C, 41.71, H, 3.59, N, 6.08.

Example A.5

1-ethyl-5-iodo-2-nitrobenzene (8)

1.66 g (10 mmol) of 5-amino-1-ethyl-2-nitrobenzene (2) are dissolved in a mixture of 3 ml of conc. sulfuric acid and 20 ml of $H_2O$ heated to 50° C. and cooled rapidly in an ice bath. At a temperature below 5° C., the mixture is subjected to diazotisation with 760 mg (11 mmol) of sodium nitrite. After 10 minutes, a pinch of urea from a spatula is added and the mixture stirred for another 5 minutes in the ice bath. This reaction mixture is added to a solution of 2.5 g of potassium iodide (15 mmol) in 10 ml of $H_2O$ and stirred at room temperature for one hour. The reaction mixture is extracted three times with 50 ml of EE each and the combined organic phases washed once with 50 ml each of In NaOH arid $H_2O$. After drying over $Na_2SO_4$, concentration by means of a rotary evaporator is carried out. The crude product is placed on silica gel and purified by flash chromatography (40 g of silica gel, 3.5×13 cm, LM: PE). 1.57 g (5.7 mmol, 57%) of (8) are obtained as a red oil.

Physical data of (8):

DC (silica gel, PE/EE 4:1): $R_f$=0.78.

$^1$H-NMR (250 MHz, $CDCl_3$): 7.72 (d, 1H, H(6)), 7.66 (dd, 1H, H(4)), 7.58 (d, 1H, H(3)), 2.85 (q, 2H, $CH_2$), 1.25 (t, 3H, $CH_3$).

UV spectrum (MeOH), $\lambda_{max}$ [nm] (log ε): 203 (4.22), [220 (3.88)], 281 (3.87), [328 (3.22)].

$C_8H_8INO_2$ (277.06 g/mol): Calc.: C, 34.68, H, 2.91, N, 5.06, found.: C, 34.84, H, 2.92, N, 4.90.

Example A.6

4-amino-2-nitro-ethylbenzene (30) [II]

[II] A. Kövendi and M. Kircz, Chem. Ber., 97, 1896 (1964)

380 ml of conc. sulfuric acid (d 1.84 g/ml) are cooled to 8° C. in a 1 liter 3-neck-flask with a KPG stirrer, internal thermometer and dropping funnel. 60.59 g (62 ml, 0.5 mol) of 4-ethylaniline are slowly added dropwise so that the temperature remains constant. After completion of the dropwise addition, the mixture is cooled to −5° C. Meanwhile, 54 ml of conc. sulfuric acid (1.84 g/ml) are added to 23 ml of 100% nitric acid (1.52 g/ml) while cooling with ice. This mixture is then slowly added dropwise to the 4-ethylaniline solution so that the temperature is held between −5 and 0° C. Stirring is continued at this temperature for 45 min. After that, the mixture is poured on ice and the precipitate removed by suction. The precipitate is suspended in 500 ml of $H_2O$, heated to 50° C. and $NH_3$ introduced for a sufficient time until a pH of 8 is reached. Cooling in an ice bath is necessary to hold the temperature between 50 and 60° C. A dark brown oil is separated which crystallises at 10° C. The precipitate is removed by suction and dried over $CaCl_2$ in a desiccator. 57.7 g (0.35 mol, 70%) of (30) are obtained as a brown solid which is used without purification.

Physical data of (30):

M.P.: 30–31° C. (Lit. [2]: 44–45° C.).

DC (silica gel, tol/EE 3:1): $R_f$=0.34.

$^1$H-NMR (250 MHz, $CDCl_3$): 7.10 (d, 1H, H(6)), 7.03 (d, 1H, H(3)), 6.80 (dd, 1H, H(5)), 5.54 (s, 2H, $NH_2$), 2.60 (q, 2H, $CH_2$), 1.10 (t, 3H, $CH_3$).

Example A.7

4-acetamido-1-ethyl-2-nitobenzene (31) [III]

[III] O. L. Brady, J. N. E. Day und P. S. Allam, J. Chem. Soc., 978 (1928)

50 g (0.3 mol) of 4-amino-1-ethyl-2-nitrobenzene (30) are added to 250 ml of ice-cold acetic acid anhydride. The mixture is stirred at room temperature for 90 min. and poured onto ice. The precipitate is removed by suction and dried over KOH in a desiccator. 58.18 g (0.28 mmol, 93%) of (31) are obtained as an almost colourless solid.

Physical data of (31):

M.P.: 112–113° C. (Lit. [III]: 111° C.).

DC (silica gel, PE/EE 1:1): $R_f$=0.35.

$^1$H-NMR (250 MHz, $CDCl_3$): 8.01 (d, 1H, H(3)), 7.71 (dd, 1H, H(5)), 7.62 (s(br.), 1H, NH), 7.27 (d, 1H, H(6)), 2.84 (q, 2H, $CH_2$), 2.19 (s, 3H, $C(O)CH_3$), 1.23 (t, 3H, $CH_3$).

UV spectrum (MeOH), $\lambda_{max}$ [nm] (log ε): 202 (4.23), 241 (4.39), 333 (3.21).

Example A.8

4-amino-1-ethyl-2,3-dinitrobenzene (32) and 4-amino-1-ethyl-2,5-dinitrobenzene (33) [III]

[III] O. L. Brady, J. N. E. Day und P. S. Allam, J. Chem. Soc., 978 (1928)

20.3 g (0.1 mol) of 4-acetamido-1-ethyl-2-nitrobenzene (31) are added to a mixture of 80 ml of 65% nitric acid and 80 ml of conc. sulfuric acid. After three days of stirring at room temperature, the mixture is poured on ice. The precipitate is removed by suction, taken up in $CH_2Cl_2$, 100 ml $H_2O$ added thereto and the mixture neutralised with solid $Na_2CO_3$. The organic phase is dried over $Na_2SO_4$ and subjected to concentration by means of a rotary evaporator. The crude product thus obtained (20.6 g, 81 mmol, 81%) is suspended in 200 ml of ethanol and heated with 2 g of solid sodium hydroxide for 40 minutes until it boils. After cooling, the reaction mixture is subjected to concentration by means of a rotary evaporator together with 28 g of silica gel until dry. Purification is carried out by flash chromatography (140 g of silica gel, 6×14 cm, LM:PE/EE, cond.: 7:1, gradient: from 7:1 to 2:1). 1.75 g (8 mmol, 8%) of (33) are obtained as an orange-red solid and 12.5 g (60 mmol, 60%) of (32) as an orange solid.

Physical data of (32):

M.P.: 122–123° C. (Lit. [III]: 125° C.).

DC (silica gel, PE/EE 1:1): $R_f$=0.50.

$^1$H-NMR (250 MHz, CDCl$_3$): 7.26 (d, 1H, arom. H), 6.90 (d, 1H, arom. H), 6.03 (s(br.), 2H, NH$_2$), 2.45 (q, 2H, CH$_2$), 1.18 (t, 3H, CH$_3$).

UV spectrum (MeOH), $\lambda_{max}$ [nm] (log $\epsilon$): 202 (4.18), 227 (4.37), [265 (3.59)], 411 (3.75).

Physical data of (33):

M.P.: 124–125° C. (Lit. [III]: 121.6° C.)

DC (silica gel, PE/EE 1:1): $R_f$=0.85.

$^1$H-NMR (250 MHz, CDCl$_3$): 8.11 (s, 1H, arom. H), 7.27 (s, 1H, arom. H), 6.07 (s(br.), 2H, NH$_2$), 2.75 (q, 2H, CH$_2$), 1.24 (t, 3H, CH$_3$).

UV spectrum (MeOH), $\lambda_{max}$ [nm] (log $\epsilon$): 226 (4.39), [243 (4.16)], [266 (3.86)], 422 (3.71).

Example A.9

1-ethyl-2,5-dinitrobenzene (34) [III, IV]

[III] O. L. Brady, J. N. E. Day und P. S. Allam, J. Chem. Soc., 978 (1928)
[IV] M. M. A. F. Holleman und J. Böeseken, Rec. Trav. Chim., 16, 425 (1897)

4 g (19 mmol) of 4-amino-1-ethyl-2,5-dinitrobenzene (33) are dissolved in 50 ml of conc. sulfuric acid. Then 50 ml of H$_2$O are added with severe cooling. 1.45 g (18 mmol) sodium nitrite in 15 ml H$_2$O are slowly added dropwise (reaction temperture below 10° C. After completion of the addition, the reaction mixture is stirred in an ice bath for 10 minutes and then fed into 100 ml of boiling EtOH. After 50 min. at reflux, the mixture is allowed to cool, poured onto ice and extracted once with 200 ml and three times with 100 ml each of Et$_2$O. The combined organic phases are washed once with 200 ml. of sat. NaHCO$_3$ solution and the aqueous phase reextracted with 50 ml of Et$_2$O. After drying over Na$_2$SO$_4$, the mixture is subjected to concentration by means of a rotary evaporator and the crude product (3.55 g of red oil applied to 4 g of silica gel) purified by flash chromatography (67 g of silica gel, 4×12 cm, LM: PE/EE 8:1). 2.64 g (13 mmol, 71%) of (34) are obtained as a yellow-orange solid.

Physical data of (34):

M.P.: 57–60° C. (Lit. [III]: 57.4–59.9° C.).

DC (silica gel, PE/EE 4:1): $R_f$=0.60.

$^1$H-NMR (250 MHz, CDCl$_3$): 8.24 (d, 1H, H(6)), 8.16 (dd, 1H, H(4)), 7.95 (d, 1H, H(3)), 2.95 (q, 2H, CH$_2$), 1.34 (t, 3H, CH$_3$).

UV spectrum (MeOH), $\lambda_{max}$ [nm] (log $\epsilon$): 204 (4.26), 257 (4.02), [298 (3.37)], [332 (3.06)].

B. Synthesis of Alcohols

General Instructions 1 (Allgemeine Arbeitsvorschrift=AAV) for Reacting Paraformaldehyde AAV 1: 5 mmol of educt are dissolved with 5 mmol of paraformaldehyde in 10 ml of DMSO (for synthesis, dried over a molecular sieve). When 0.05 to 0.5 mmol of potassium-tert-butylate in 3 ml of tert-butanol are added, the colour changes from yellow to purple. After 15 min. of stirring at room temperature and 2 hours at 80° C., the solution is allowed to cool, neutralised with approx. 4 drops of conc. HCl, diluted with 25 ml of saturated NaCl solution and extracted three times with 20 ml each of acetic acid ethyl ester. The combined organic phases are dried over Na$_2$SO$_4$, filtered off and concentrated by means of a rotary evaporator. The crude product is purified by flash chromatography (45 g of silica gel, 4×12 cm, LM:Tol/EE, cond.:tol.; gradient:tol, until unreacted educt is separated, then 15:1 or 8:1).

AAV 1.2: Repeat AAV 1 except that DMF instead of DMSO is used as the solvent and the reaction time is increased to 3 hrs. at 90° C.

Example B.1

2-(5-chloro-2-nitrophenyl)propanol (9)

According to AAV 1: 895 mg (4.8 mmol) of 5-chloro-1-ethyl-2-nitrobenzene (6), 160 mg (5.3 mmol) of paraformaldehyde in 10 ml DMSO and 76 mg (0.7 mmol) of potassium tert.-butylate in 4 ml tert.-butanol.

Yield: 870 mg (4.03 mmol, 84%) of (9) as a yellow oil.

Physical data of (9):

DC (silica gel, PE/EE 4:1): $R_f$=0.27.

$^1$H-NMR (250 MHz, CDCl$_3$): 7.72 (d, 1H, H(3)), 7.45 (d, 1H, H(6)), 7.30 (dd, 1H, H(4)), 3.74 (m, 2H, α-CH$_2$), 3.54 (sextet, 1H, β-CH), 1.71 (s(br.), 1H, OH), 1.30 (d, 3H, CH$_3$).

UV spectrum (MeOH), $\lambda_{max}$ [nm] (log $\epsilon$): 206 (4.17), 216 (4.06), 262 (3.76), [328 (2.95)].

C$_9$H$_{10}$ClNO$_3$ (215.64 g/mol): Calc.: C, 50.13, H, 4.67, N, 6.50; found.: C, 50.20, H, 4.75, N, 6.20.

Example B.2

2-(5-bromo-2-nitrophenyl)propanol (10)

According to AAV 1: 1.39 g (6 mmol) of 5-bromo-1-ethyl-2-nitrobenzene (7), 210 mg (7 mmol) of paraformaldehyde in 10 ml DMSO and 100 mg (0.89 mmol) of potassium tert.-butylate in 4 ml of tert.-butanol.

Yield: 1.32 g (5.01 mmol, 85%) of (10) as a yellow oil.

Physical data of (10):

DC (silica gel, PE/EE 7:3): $R_f$=0.57.

$^1$H-NMR (250 MHz, CDCl$_3$): 7.63 (m, 2H, H(3), H(6)), 7.47 (dd, 1H, H(4)), 3.74 (m, 2H, α-CH$_2$), 3.52 (sextet, 1H, β-CH), 1.68 (s(br.), 1H, OH), 1.30(d, 3H, CH$_3$).

UV spectrum (MeOH), $\lambda_{max}$ [nm] (log $\epsilon$): 202 (4.16), [218 (3.95)], 263 (3.76), [330 (2.96)].

C$_9$H$_{10}$BrNO$_3$ (260.09 g/mol): Calc.: C, 41.56, H, 3.88, N, 5,39; found: C, 41.74, H, 3.95, N, 5.27.

Example B.3

2-(5-iodo-2-nitrophenyl)propanol (11)

According to AAV 1: 1.45 g (5 mmol) of 5-iodo-1-ethyl-2-nitrobenzene (8), 165 mg (5.5 mmol) of paraformaldehyde in 10 ml of DMSO and 80 mg (0.7 mmol) of potassium tert.-butylate in 4 ml of tert.-butanol.

Yield: 1.36 g (4.4 mmol, 85%) of (11) as a yellow solid.

Physical data of (11):

DC (silica gel, PE/EE 4:1): $R_f$=0.29.

$^1$H-NMR (250 MHz, CDCl$_3$): 7.81 (d, 1H, H(6)), 7.69 (dd, 1H, H(4)), 7.46 (d, 1H, H(3)), 3.76 (m, 2H, α-CH$_2$), 3.48 (sextet, 1H, β-CH), 1.54 (s(br.), 1H, OH), 1.29 (d, 3H, CH$_3$).

UV spectrum (MeOH), $\lambda_{max}$ [nm] (log $\epsilon$): 204 (4.29), [222 (3.93)], 274 (3.8), [335 (3.18)].

C$_9$H$_{10}$INO$_3$ (307.08 g/mol): Calc.: C, 35.17, H, 3.28, N, 4.56; found: C, 35.18, H, 3.27, N, 4.06.

Example B.4

2-(2,5-dinitrophenyl)propanol (35)

According to AAV 1.2: 1.44 g (7 mmol) of 1-ethyl-2,5-dinitrobenzene (34), 662 mg (22 mmol) of paraformaldehyde in 10 ml DMF und 200 mg (1.8 mmol) of potassium tert.-butylate in 4 ml of tert.-butanol.

Yield: 628 mg (3.2 mmol, 46%) of educt (34) and 394 mg (1.74 mmol, 25%) of (35) as a yellow solid. 100 mg of (35) are recrystallised from 15 ml of H$_2$O/EtOH 4:1 for analysis.

Physical data of (35):

M.P.: 82–83° C.

DC (silica gel, PE/EE 7:3): $R_f$=0.45.

$^1$H-NMR (250 MHz, CDCl$_3$): 8.38 (d, 1H, H(6)), 8.19 (dd, 1H, H(4)), 7.84 (d, 1H, H(3)), 3.90–3.72 (m, 2H, 2×α-CH), 3.52 (sextet, 1H, β-CH), 1.55 (t, 1H, OH), 1.38 (d, 3H, CH$_3$).

UV spectrum (MeOH), $\lambda_{max}$ [nm] (log ε): 205 (4.24), 256 (4.00), [289 (3.41)], [334 (3.04)].

$C_9H_{10}N_2O_5$ (226.19 g/mol): Calc.: C, 47.79, H, 4.46, N, 12.39; found: C, 48.01, H, 4.42, N, 12.33.

C. Synthesis of the Protective Group Reagents
General Instructions (AAV) 2 for Synthesising Protective Group Reagents AAV 2: Over 5 min., a solution of 5 mmol of alcohol and 5 mmol of triethyl amine in 8 ml of THF is added dropwise to a solution of 6 mmol of chloroformic acid trichloromethyl ester (1.2-fold excess) cooled to 0° C. in 8 ml of THF (dist. over $CaH_2$). After stirring in an a ice bath for 1 to 2 hours (DC control), the reaction solution is removed by suction over diatomeceous earth, post-washed with some THF and any excess reagent removed by rotation. The protective group reagents thus obtained are dried on a high-vaccum pump for 1 or 2 hours and kept in a refrigerator under argon.

Example C.1
2-(5-chloro-2-nitrophenyl)propoxy carbonyl chloride (12)

According to AAV 2: 914 mg (560 μl, 4.6 mmol) of chloroformic acid trichloromethylester in 4 ml of abs. THF, 664 mg (3.1 mmol) 2-(5-chloro-2-nitrophenyl)-propanol (9) und 311 mg (425 μl, 3.1 mmol) of triethylamine in 4 ml of abs. THF.

Yield: 838 mg (3 mmol, 97%) of (12) as a yellow oil.
Physical data of (12):
DC (silica gel, $CH_2Cl_2$): $R_f$=0.93.
$^1$H-NMR (250 MHz, $CDCl_3$): 7.81 (d, 1H, H(3)), 7.39 (m, 2H, H(6), H(4)), 4.45 (m, 2H, α-$CH_2$), 3.84 (sextet, 1H, β-CH), 1.39 (d, 3H, $CH_3$).

Example C.2
2-(5-bromo-2-nitrophenyl)propoxy carbonyl chloride (13)

According to AAV 2: 742 mg (455 μl, 3.8 mmol) of chloroformic acid trichloromethylester in 4 ml of abs. THF, 653 mg (2.5 mmol) of 2-(5-bromo-2-nitrophenyl)propanol (10) and 254 mg (350 μl, 2.5 mmol) of triethylamine in 4 ml of abs. THF. Yield: 805 mg (2.49 mmol, 99%) of (13) as a yellow oil.

Physical data of (13):
DC (silica gel, $CH_2Cl_2$): $R_f$=0.92.
$^1$H-NMR (250 MHz, $CDCl_3$): 7.72 (d, 1H, H(3)), 7.55 (m, 2H, H(6), H(4)), 4.45 (m, 2H, α-$CH_2$), 3.80 (sextet, 1H, β-CH), 1.39 (d, 3H, $CH_3$).

Example C.3
2-(5-iodo-2-nitrophenyl)propoxy carbonyl chloride (14)

According to AAV 2: 760 mg (465 μl, 3.8 mmol) of chloroformic acid trichloromethylester in 4 ml of abs. THF, 787 mg (2.6 mmol) of 2-(5-iodo-2-nitrophenyl)-propanol (11) and 259 mg (355 μl, 2.6 mmol) of triethylamine in 4 ml of abs. THF.

Yield: 666 mg (1.8 mmol, 95%) of (14) as a yellow oil.
Physical data of (14):
DC (silica gel, $CH_2Cl_2$): $R_f$=0.91.
$^1$H-NMR (250 MHz, $CDCl_3$): 7.75 (m, 2H, H(6), H(4)), 7.53 (d, 1H, H(3)), 4.44 (m, 2H, α-$CH_2$), 3.74 (sextet, 1H, β-CH), 1.38 (d, 3H, $CH_3$).

Example C.4
2-(2,5-dinitrophenyl)propoxy carbonyl chloride (36)

According to AAV 2: 237 mg (145 μl, 1.2 mmol) of chloroformic acid trichloromethyl ester in 4 ml of abs. THF, 226 mg (1 mmol) of 2-(2,5-dinitrophenyl)propanol (35) and 101 mg (140 μl, 1 mmol) of triethylamine in 4 ml of abs. THF.

Yield: 320 mg (1.1 mmol, 110%) of slighly contaminated (36) as a yellow oil.
Physical data of (36):
DC (silica gel, $CH_2Cl_2$): $R_f$=0.98.
$^1$H-NMR (250 MHz, $CDCl_3$): 8.34 (d, 1H, H(6)), 8.27 (dd, 1H, H(4)), 7.93 (d, 1H, H(3)), 4.43 (m, 2H, 2×α-CH), 3.76 (sextet, 1H, β-CH), 1.46 (d, 3H, $CH_3$).

D. Synthesis of the 5'-O-protected 2'-deoxynucleosides
General Instructions (AAV) 3 for Introducing Protective Group Reagents Into the 5'-O Position of the 2'-deoxynucleosides 3 AAV 3: 1 mmol of nucleoside is co-evaporated three times with 3 ml each of abs. pyridine, dissolved in 3 ml of abs. pyridine and cooled to −50° C. Then a 1.25 to 1.75-fold excess of the protective group reagent in 3 ml. of abs. $CH_2Cl_2$ is added dropwise over 15 min. After 5.5 hours of stirring at a temperature between −60° C. and −30° C., ultimately −15° C., the reaction solution is diluted with 10 ml of $H_2O$ and the aqueous phase extracted three times with 10 ml each of $CH_2Cl_2$. The combined organic phases are dried over $Na_2SO_4$, subjected to concentration by means of a rotary evaporator and co-evaporated three times with toluene in order to remove all of the pyridine. The crude product thus obtained is purified over a silica gel column by means of flash chromatography (20 g of silica gel, 2×14 cm, LM: $CH_2Cl_2$/MeOH, cond.: $CH_2Cl_2$, gradient: 100 ml of $CH_2Cl_2$, 100 ml each 100:1, 100:2, 100:3, 100:3.5 and 100:4). The relevant product fractions are subjected to concentration by means of a rotary evaporator and the foams obtained dried in a high vaccum at 35° C.

Example D.1
5'-O-[2-(5-chloro-2-nitrophenyl)propoxycarbonyl] thymidine (15),
  bis-[2-(5-chloro-2-nitrophenyl)propyl]carbonate (16),
  3',5'-di-O-[2-(5-chloro-2-nitrophenyl)propoxycarbonyl] thymidine (17),
  and 3'-O-[2-(5-chloro-2-nitrophenyl)propoxycarbonyl)] thymidine (18)

According to AAV 3: 970 mg (4 mmol) of thymidine/15 ml of abs. pyridine, 1.5 g (5 mmol) of 2-(5-chloro-2-nitrophenyl)propoxy carbonyl chloride (12)/15 ml abs. $CH_2Cl_2$.

Yield: 359 mg (0.8 mmol, 30%) of (16) as a yellow solid, 173 mg (0.24 mmol, 6%) of (17), 70 mg (0.14 mmol, 4%) of (18) and 1.34 (2.8 mmol, 69%) of (15) as colourless foams.

Physical data of (15):
DC (silica gel, Tol/EE/MeOH 5:4:1): $R_f$=0.40.
$^1$H-NMR (250 MHz, $CDCl_3$): 8.75 (s(br.), 1H, NH), 7.74 (d, 1H, arom. H NPPOC), 7.41 (d, 1H, arom. H NPPOC), 7.34 (dd, 1H, arom. H NPPOC), 7.29 (s, 1H, H—C(6)), 6.31 (m, 1H, H—C(1')), 4.47–4.08 (m, 6H, α-$CH_2$ NPPOC, H—C(3'), 2×H—C(5'), H—C(4')), 3.82 (m, 1H, β-CH NPPOC), 2.66 (d(br), 1H, OH—C(3')), 2.37 (m, 1H, H—C(2')), 2.17 (m, 1H, H—C(2')), 1.80 (dd, 3H, $CH_3$ Thy), 1.34 (d, 3H, $CH_3$ NPPOC).

UV spectrum (MeOH), $\lambda_{max}$ [nm] (log ε): 207 (4.32), 263 (4.15), [335 (2.92)].

$C_{20}H_{22}ClN_3O_9$ (483.86 g/mol): Calc.: C, 49.65, H, 4.58, N, 8.68; found: C, 49.31, H, 4.57, N, 8.54.

Physical data of (16):
M.P.: 95–100° C.
DC (silica gel, Tol/EE/MeOH 5:4:1): $R_f$=0.94.
$^1$H-NMR (250 MHz, $CDCl_3$): 7.75 (d, 2H, 2×H(3)), 7.40 (m, 2H, 2×H(6)), 7.33 (m, 2H, 2×H(4)), 4.32–4.15 (m, 4H, 2×α-$CH_2$), 3.75 (m, 2H, 2×β-CH), 1.33 (2×d, 6H, 2×$CH_3$).

UV spectrum (MeOH), $\lambda_{max}$ [nm] (log ε): 203 (4.42), [215 (4.26)], 260 (4.07), [334 (3.23)].

$C_{19}H_{18}Cl_2N_2O_7$ (457.27 g/mol): Calc.: C, 49.91, H, 3.97, N, 6.13; found: C, 49.93, H, 3.99, N, 6.11.

Physical data of (17):

DC (silica gel, Tol/EE/MeOH 5:4:1): $R_f$=0.79.

$^1$H-NMR (250 MHz, CDCl$_3$): 8.03(s(br.), 1H, NH), 7.76 (m, 2H, 2×arom. H NPPOC), 7.37 (m, 4H, 4×arom. H NPPOC), 7.26 (s, 1H, H—C(6)), 6.32 (m, 1H, H—C(1')), 5.11 (m, 1H, H—C(3')), 4.46–4.12 (m, 7H, 2×α-CH$_2$ NPPOC, 2×H—C(5')), H—C(4')), 3.82 (m, 2H, 2×β-CH NPPOC), 2.46 (m, 1H, H—C(2')), 2.22 (m, 1H, H—C(2')), 1.80 (d, 3H, CH$_3$ Thy), 1.36 (d, 6H, 2×CH$_3$ NPOOC).

UV spectrum (MeOH), $\lambda_{max}$ [nm] (log ε): 207 (4.64), 262 (4.32), [327 (3.34)].

$C_{30}H_{30}Cl_2N_4O_{13}$ (725.49 g/mol): Calc.: C, 49.67, H, 4.17, N, 7.72; found.: C, 49.55, H, 4.32, N, 7.42.

Physical data of (18):

DC (silica gel, Tol/EE/MeOH 5:4:1): $R_f$=0.55.

$^1$H-NMR (250 MHz, CDCl$_3$): 8.31(s(br.), 1H, NH), 7.78 (dd, 1H, arom. H NPPOC), 7.40 (m, 3H, 2×arom. H NPPOC, H—C(6)), 6.12 (m, 1H, H—C(1')), 5.23 (m, 1H, H(3')), 4.38 (m, 1H, H—C(4')), 4.24–4.11 (m, 2H, α-CH$_2$ NPPOC), 3.84 (m, 3H, 2×H—C(5'), β-CH NPPOC), 2.59–2.36 (m, 3H, OH—C(5'), 2×H—C(2')), 1.90 (s, 3H, CH$_3$ Thy), 1.36(d, 3H, CH$_3$ NPOOC).

UV spectrum (MeOH) $\lambda_{max}$ [nm] (log ε): 207 (4.37), 263 (4.17), [331 (2.96)].

$C_{20}H_{22}ClN_3O_9$ (483.86 g/mol): Calc.: C, 49.65, H, 4.58, N, 8.68; found: C, 49.58, H, 4.70, N, 8.02.

Example D.2

5'-O-[2-(5-bromo-2-nitrophenyl)propoxycarbonyl]thymidine (19), bis-[2-(5-bromo-2-nitrophenyl)propyl]carbonate (20), 3',5'-di-O-[2-(5-bromo-2-nitrophenyl)propoxycarbonyl]thymidine (21), and 3'-O-[2-(5-bromo-2-nitrophenyl)propoxycarbonyl]thymidine (22).

According to AAV 3: 1.18 g (4.9 mmol) of thymidine/20 ml of abs. pyridine, 2.1 g (6.6 mmol) of 2-(5-bromo-2-nitrophenyl)propoxy carbonyl chloride (13)/20 ml of abs. CH$_2$Cl$_2$.

Yield: 280 mg (0.5 mmol, 16%) of (20) as a bright yellow solid, 458 mg (0.56 mmol, 12%) of (21), 48 mg (0.1 mmol, 2%) of (22) and 1.89 g (3.6 mmol, 74%) of (19) as colourless foams.

Physical data of (19):

DC (silica gel, Tol/EE/MeOH 5:4:1): $R_f$=0.42.

$^1$H-NMR (250 MHz, CDCl$_3$): 8.71 (s(br.), 1H, NM, 7.65 (d, 1H, arom. H NPPOC), 7.57 (d, 1H, arom. H NPPOC), 7.51 (dd, 1H, arom. H NPPOC), 7.29 (s, 1H, H—C(6)), 6.31 (m, 1H, H—C(1')), 5.28–4.11 (m, 6H, α-CH$_2$ NPPOC, H—C(3'), 2×H—C(5'), H—C(4')), 3.80 (m, 1H, β-CH NPPOC), 2.64 (s(br), 1H, OH—C(3')), 2.37 (m, 1H, H—C (2')), 2.05 (m, 1H, H—C(2')), 1.80 (d, 3H, CH$_3$ Thy), 1.35 (d, 3H, CH$_3$ NPPOC).

UV spectrum (MeOH), $\lambda_{max}$ [nm] (log ε): 205 (4.41), 265 (4.18), [337 (2.95)].

$C_{20}H_{22}BrN_3O_9$ (528.32 g/mol): Calc.: C, 45.47, H, 4.20, N, 7.95; found: C, 45.09, H, 4.14, N, 7.54.

Physical data of (20):

M.P.: 92–97° C.

DC (silica gel, Tol/EE/MeOH 5:4:1): $R_f$=0.93.

$^1$H-NMR (250 MHz, CDCl$_3$): 7.66 (d, 2H, 2×H(3)), 7.56 (d, 2H, 2×H(6)), 7.48 (m, 2H, 2×H(4)), 4.32–4.15 (m, 4H, 2×α-CH$_2$), 3.71 (sextet, 2H, 2×β-CH), 1.33 (2×d, 6H, 2×CH$_3$) UV spectrum (MeOH), $\lambda_{max}$ [nm] (log ε): 202 (4.49), [218 (4.26)], 263 (4.11), [334 (3.28)].

$C_{19}H_{18}Br_2N_2O_7$ (546.18 g/mol): Calc.: C, 41.78, H, 3.32, N, 5.13; found: C, 42.01, H, 3.35, N, 4.96.

Physical data of (21):

DC (silica gel, Tol/EE/MeOH 5:4:1): $R_f$=0.78.

$^1$H-NMR (250 MHz, CDCl$_3$): 8.12 (s(br.), 1H, NH), 7.67 (m, 2H, 2×arom. H NPPOC), 7.53 (m, 4H, 4×arom. H NPPOC), 7.26 (m, 1H, H—C(6)), 6.33 (m, 1H, H—C(1')), 5.11 (m, 1H, H—C(3')), 4.46–4.11 (m, 7H, 2×α-CH$_2$ NPPOC, 2×H—C(5'), H—C(4')), 3.79 (m, 2H, 2×, β-CH NPPOC), 2.46 (m, 1H, H—C(2')), 2.22 (m, 1H, H—C(2')), 1.80 (d, 3H, CH$_3$ Thy), 1.35 (d, 6H, 2×CH$_3$ NPPOC).

UV spectrum (MeOH), $\lambda_{max}$ [nm] (log ε): 202 (4.61), [216 (4.42)], 263 (4.34), [333 (3.33)].

$C_{30}H_{30}Br_2N_4O_{13}$ (814.40 g/mol): Calc.: C, 44.24, H, 3.71, N, 6.88; found: C, 44.28, H, 3.72, N, 6.80.

Physical data of (22):

DC (silica gel, Tol/EE/MeOH 5:4:1): $R_f$=0.54.

$^1$H-NMR (250 MHz, CDCl$_3$): 7.98 (s(br.), 1H, NH), 7.69 (dd, 1H, arom. H NPPOC), 7.58 (d, 1H, arom. H NPPOC), 7.52 (dd, 1H, arom. H NPPOC), 7.38 (dd, 1H, H—C(6)), 6.12 (m, 1H, H—C(1')), 5.23 (m, 1H, H—C(3')), 4.38 (m, 1H—C(4')), 4.24–4.10 (m, 2H, α-CH$_2$ NPPOC) 3.91–3.74 (m, 3H, 2×H—C(5'), β-CH NPPOC), 2.56–2.34 (m, 2H, 2×H—C(2')), OH—C(5') not visible, 1.91 (s, 3H, CH$_3$ Thy), 1.36 (d, 3H, CH$_3$ NPPOC).

UV spectrum (MeOH), $\lambda_{max}$ [nm] (log ε): 202 (4.36), 264 (4.18), [333 (3.02)].

$C_{20}H_{22}BrN_3O_9$ (528.32 g/mol): Calc: C, 45.47, H, 4.20, N, 7.95; found: C, 45.15, H, 4.21, N, 7.57.

Example D.3

5'-O-[2-(5-iodo-2-nitrophenyl)propoxycarbonyl]thymidine (23), bis-[2-(5-iodo-2-nitrophenyl)propyl]carbonate (24), 3',5'-di-O-[2-(5-iodo-2-nitrophenyl)propoxycarbonyl]thymidine (25), and 3'-O-[2-(5-iodo-2-nitrophenyl)propoxycarbonyl]thymidine (26)

According to AAV 3: 1.12 g (4.6 mmol) of thymidine/20 ml of abs. pyridine, 2.3 g (6.2 mmol) of 2-(5-iodo-2-nitrophenyl)propoxy carbonyl chloride (14)/20 ml of abs. CH$_2$Cl$_2$.

Yield: 502 mg. (0.8 mmol, 25%) of (24) as an almost colourless solid, 458 mg (0.5 mmol, 11%) of (25), 75 mg (0.13 mmol, 3%) of (26) and 1.93 g (3.4 mmol, 73%) of (23) as colourless foams.

Physical data of (23):

DC (silica gel, Tol/EE/MeOH 5:4:1): $R_f$=0.46.

$^1$H-NMR (250 MHz, CDCl$_3$): 8.51 (s(br.), 1H, NH), 7.74 (m, 2H, 2×arom. H NPPOC), 7.47 (d, 1 H, arom. H NPPOC), 7.29 (d, 1H, H—C(6)), 6.31 (t, 1H, H—C(1')), 4.46–4.10 (m, 6H, α-CH$_2$ NPPOC, H—C(3'), 2×H—C(5'), H—C(4')), 3.75 (m, 1H, β-CH NPPOC), 2.49 (s(br), 1H, OH—C(3')), 2.37 (m, 1H, H—C(2')), 2.18 (m, 1H, H—C (2')), 1.80 (m, 3H, CH$_3$ Thy), 1.35 (d, 3H, CH$_3$ NPPOC).

UV spectrum (MeOH), $\lambda_{max}$ [nm] (log c): 204 (4.41), 267 (4.16), [335 (3.19)].

$C_{20}H_{22}IN_3O_9$ (575.31 g/mol): Calc.: C, 41.76, H, 3.85, N, 7.30, found: C, 41.46, H, 3.88, N, 7.18.

Physical data of (24):

M.P.: 104–115° C.

DC (silica gel, Tol/EE/MeOH 5:4:1): $R_f$=0.94.

$^1$H-NMR (250 MHz, CDCl$_3$): 7.76 (s, 2H, 2×H(6)), 7.71 (d, 2H, 2×H(4)), 7.49 (d, 2H, 2×H(3)), 4.29 (m, 2H, α-CH$_2$), 4.17 (m, 2H, β-CH$_2$), 3.68 (sextet, 2H, 2×β-CH), 1.34 (d, 6H, 2×CH$_3$).

UV spectrum (MeOH), $\lambda_{max}$ [nm] (log ε): 203 (4.57), [219 (4.26)], 276 (4.07), [332 (3.47)].

$C_{19}H_{18}I_2N_2O_7$ (640.16 g/mol): Calc.: C, 35.65, H, 2.83, N, 4.38; found: C, 36.04, H, 3.06, N, 4.07.

Physical data of (25):

DC (silica gel, Tol/EE/MeOH 5:4:1): $R_f$=0.84.

$^1$H-NMR (250 MHz, CDCl$_3$): 8.26 (s(br.), 1H, NH), 7.74 (m, 4H, 4×arom. H NPPOC), 7.49 (m, 2H, 2×arom. H NPPOC), 7.27 (m, 1H, H—C(6)), 6.34 (m, 1H, H—C(1')), 5.12 (m, 1H, H—C(3')), 4.45–4.10 (m, 7H, 2×α-CH$_2$ NPPOC, 2×H—C(5'), H—C(4')), 3.75 (m, 2H, 2×β-CH NPPOC), 2.45 (m, 1H, H—C(2')), 2.24 (m, 1H, H—C(2')), 1.80 (d, 3H, CH$_3$ Thy), 1.35 (d, 6H, 2×CH$_3$ NPPOC).

UV spectrum (MeOH), $\lambda_{max}$ [nm] (log ε): 202 (4.69), 267 (4.30), [333 (3.45)].

$C_{30}H_{30}I_2N_4O_{13}$ (908.38 g/mol): Calc.: C, 39.67, H, 3.33, N, 6.17; found: C, 39.61, H, 3.39, N, 5.99.

Physical data of (26):

DC (silica gel, Tol/EE/MeOH 5:4:1): $R_f$=0.53.

$^1$H-NMR (250 MHz, CDCl$_3$): 7.78 (s(br.), 1H, NH), 7.73 (m, 2H, 2×arom. H NPPOC), 7.51 (dd, 1H, arom. H NPPOC), 7.39 (dd, 1H, H—C(6)), 6.12 (m, 1H, H—C(1')), 5.23 (m, 1H, H—C(3')), 4.36 (m, 1H, α-CH NPPOC), 4.20 (m, 1H, α-CH NPPOC), 4.13 (m, 1H, H—C(4')), 3.87 (m, 2H, 2×H—C(5')), 3.74 (sextet, 1H, β-CH NPPOC), 2.56–2.39 (m, 3H, OH—C(5'), 2×H—C(2')), 1.91 (s, 3H, CH$_3$ Thy), 1.35 (d, 3H, CH$_3$ NPPOC).

UV spectrum (MeOH), $\lambda_{max}$ [nm] (log ε): 202 (4.49), 267 (4.17), [333 (3.19)].

$C_{20}H_{22}IN_3O_9$ (575.31 g/mol): Calc.: C, 41.76, H, 3.85, N, 7.30; found: C, 42.22, H, 3.85, N, 7.20.

Example D.4

5'-O-[2-(2,5-dinitrophenyl)propoxycarbonyl]thymidine (37) and bis[2-(2,5-dinitrophenyl)propyl]carbonate (38)

According to AAV 3: 180 mg (0.74 mmol) of thymidine/3 ml of abs. pyridine, 320 mg (I mmol) of 2-(2,5-dinitrophenyl)propoxy carbonyl chloride (36)/3 ml of abs. CH$_2$Cl$_2$.

Yield: 48 mg (0.1 mmol, 10%) of (38) as a yellow solid and 250 mg (0.51 mmol, 68%) of (37) as colourless foam.

Physical data of (37):

DC (silica gel, Tol/EE/MeOH 5:4:1): $R_f$=0.34.

$^1$H-NMR (250 MHz, CDCl$_3$): 9.11 (s(br), 1H, NH), 8.33 (d, 1H, H(6) NPPOC), 8.23 (m, 1 H, H(4) NPPOC), 7.87 (dd, 1H, H(3) NPPOC), 7.27 (s, 1H, H—C(6)), 6.28 (t, 1H, H—C(1')), 4.51–4.17 (m, 5H, 2×α-CH NPPOC, H—C(3'), 2×H—C(5')), 4.10 (m, 1H, H—C(4')), 3.74 (m, 1H, β-CH NPPOC), 3.03 (m(br), 1H, OH—C(3')), 2.38 (m, 1H, H—C(2')), 2.17 (m, 1H, H—C(2')), 1.79 (d, 3H, CH$_3$ Thy), 1.43 (d, 3H, CH$_3$ NPPOC).

UV spectrum (MeOH), $\lambda_{max}$ [nm] (log ε): 205 (4.47), 258 (4.26), [334 (3.02)].

$C_{20}H_{22}N_4O_{11}\times0.5\ H_2O$ (503.42 g/mol): Calc.: C, 47.71, H, 4.60, N, 11.13; found: C, 48.08, H, 4.67, N, 11.01.

Example D.5

5'-O-[2-(5-chloro-2-nitrophenyl)propoxycarbonyl]-N$^6$-phenyloxyacetyl-2'-deoxyadenosine (27)

According to AAV 3: 385 mg (1 mmol) of N$^6$-phenyloxyacetyl-2'-deoxyadenosine/3.5 ml abs. of pyridine, 403 mg (1.45 mmol) of 2-(5-chloro-2-nitrophenyl) propoxy carbonyl chloride (12)/3.5 ml of abs. CH$_2$Cl$_2$.

Yield: 463 mg (0.74 mmol, 74%) of (27) as a colourless foam.

Physical data of (27):

DC (silica gel, Tol/EE/MeOH 5:4:1): $R_f$=0.46.

$^1$H-NMR (250 MHz, CDCl$_3$): 9.40 (s(br.), 1H, NH), 8.76 u. 8.16 (2×d, 2H, H—C(2), H—C(8)), 7.74 (d, 1H, arom. H NPPOC), 7.41 (m, 1H, arom. H NPPOC), 7.32 (m, 3H, 1×arom. H NPPOC, 2×arom. H Pac), 7.04 (m, 3H, 3×arom. H Pac), 6.49 (m, 1H, H—C(1')), 4.85 (s, 2H, CH$_2$Pac), 4.72 (m, 1H, H—C(3')), 4.42–4.08 (m, 5H, α-CH$_2$ NPPOC, 2×C(5'), H—C(4')), 3.84 (m, 1H, β-CH NPPOC), 2.88 (m, 1H, H—C(2')), 2.56 (m, 1H, H—C(2')), 2.39 (s(br), 1H, OH—C(3')), 1.35 (d, 3H, CH$_3$NPPOC).

UV spectrum (MeOH), $\lambda_{max}$ [nm] (log ε): 209 (4.61), [260 (4.30)], 270 (4.38), [337 (2.94)].

$C_{28}H_{27}ClN_6O_9$ (627.01 g/mol): Calc.: C, 53.64, H, 4.34, N, 13.40, found: C, 53.44, H, 4.30, N, 13.50.

Example D.6

5'-O-[2-(5-bromo-2-nitrophenyl)propoxycarbonyl]-N$^6$-phenyloxyacetyl-2'-deoxyadenosine (28)

According to AAV 3: 319 mg (0.83 mmol) of N$^6$-phenyloxyacetyl-2'-deoxyadenosine/3 ml of abs. pyridine, 374 mg (1.16 mmol) of 2-(5-bromo-2-nitrophenyl) propoxy carbonyl chloride (13)/3 ml of abs. CH$_2$Cl$_2$.

Yield: 397 mg (0.59 mmol, 71%) (28) as a colourless foam.

Physical data of (28):

DC (silica gel, Tol/EE/MeOH 5:4:1): $R_f$=0.31.

$^1$H-NMR (250 MHz, CDCl$_3$): 9.44 (s(br.), 1H, NH), 8.75 u. 8.18 (2×d, 1H, H—C(2), H—C(8)), 7.65 (d, 1H, arom. H NPPOC), 7.58 (dd, 1H, arom. H NPPOC), 7.47 (m, 1H, arom. H NPPOC), 7.31 (m, 2H, 2×arom. H Pac), 7.02 (m, 3H, 3×arom. H Pac), 6.50 (t, 1H, H—C(1')), 4.85 (s, 2H, CH$_2$ Pac), 4.71 (m, 1H, H—C(3')), 4.44–4.08 (m, 5H, α-CH$_2$ NPPOC, 2×H—C(5'), H—C(4')), 3.80 (m, 1H, β-CH NPPOC), 2.87 (m, 1H, H—C(2')), 2.57 (m, 1H, H—C(2'), OH—C(3') (concealed), 1.35 (d, 3H, CH$_3$ NPPOC).

UV spectrum (MeOH), $\lambda_{max}$ [nm] (log ε): 209 (4.62), [258 (4.29)], 270 (4.39), 335 (3.06)

$C_{28}H_{27}BrN_6O_9$ (671.46 g/mol): Calc.: C, 50.09, H, 4.05, N, 12.52; found: C, 49.86, H, 4.04, N, 12.57.

Example D.7

5'-O-[2-(5-iodo-2-nitrophenyl)propoxycarbonyl]-N$^6$-phenyloxyacetyl-2'-deoxyadenosine (29)

According to AAV 3: 310 mg (0.8 mmol) of N$^6$-phenyloxyacetyl-2'-deoxyadenosine/3 ml of abs. pyridine, 429 mg (1.16 mmol) of 2-(5-iodo-2-nitrophenyl) propoxy carbonyl chloride (14)/3 ml of abs. CH$_2$Cl$_2$.

Yield: 451 mg (0.63 mmol, 78%) of (29) as a colourless foam.

Physical data of (29):

DC (silica gel, Tol/EE/MeOH 5:4:1): $R_f$=0.44.

$^1$H-NMR (250 MHz, CDCl$_3$): 9.43 (s(br.), 1H, NH), 8.75 and 8.18 (2×d, 2H, H—C(2), H—C(8)), 7.76 (m, 1H, arom. H NPPOC), 7.69 (m, 1H, arom. H NPPOC), 7.47 (d, 1H, arom. H NPPOC), 7.32 (m, 2H, 2×arom. H Pac), 7.02 (m, 3H, 3×arom. H Pac), 6.51 (t, 1H, H—C(1')), 4.85 (s, 2H, CH$_2$ Pac), 4.72 (m, 1H, H—C(3')), 4.44–4.07 (m, 5H, α-CH$_2$ NPPOC, 2×H—C(5'), H—C(4')), 3.75 (m, 1H, β-CH NPPOC), 2.87 (m, 1H, H—C(2')), 2.68 (s(br), 1H, OH—C(3')), 2.57 (m, 1H, H—C(2')), 1.34 (d, 3H, CH$_3$ NPPOC).

UV spectrum (MeOH), $\lambda_{max}$ [nm] (log ε): 209 (4.62), [258 (4.29)], 270 (4.39), 335 (3.06).

$C_{28}H_{27}IN_6O_9$ (718.46 g/mol): Calc.: C, 46.81, H, 3.79, N, 11.70; found: C, 46.64, H, 3.79, N, 11.73.

Irradiation Experiments

1. Execution

Nucleoside derivatives with appropriate protection were irradiated with the aid of an apparatus consisting of an Hg ultrahigh-pressure lamp (200 W), an IR filter (water), a shutter (automatic shutter for the exact regulation of the time of irradiation), a standard interference filter (filter 1) having a small range around the wavelength of 365 nm, a collector lens and a cell holder temperature-controlled at about 17° C. In order to prevent overheating of filter 1, a broad-band filter UG1 (filter 2) was optionally installed between the shutter and filter 1. Light of a wavelength of 365 nm was used for the irradiation experiments so as to ensure that only the protective group and not the heterocyclic bases are excited. Irradiation was carried out in quartz cells (3.5 ml) with 3 ml of solution in each case (solvent: methanol/water 1:1, initial concentration 0.1 mmol/l). After irradiation was completed two samples were taken from the cell and analysed with the aid of an HPLC system.

The Merck-Hitachi HPLC system consisted of the following devices: pump L-7100, auto-sampler L-7200, UV/VIS detector (detection wavelength 260 nm) L-7420 and interface D-7000. A Merck LICHROSORB RP 18 column was used. The experiment was controlled by a Compaq computer through the HSM manager.

The following gradient (solvent: water and acetonitrile) was used for chromatography (see (table 1).

TABLE 1

Gradient

| Time [min] | H$_2$O | H$_2$O/MeCN (1:1) [%] | MeCN [%] | Flow |
|---|---|---|---|---|
| 0 | 100 | 0 | 0 | 1 |
| 3 | 100 | 0 | 0 | 1 |
| 10 | 0 | 100 | 0 | 1 |
| 25 | 0 | 0 | 100 | 1 |
| 30 | 0 | 100 | 0 | 1 |
| 33 | 100 | 0 | 0 | 1 |
| 38 | 100 | 0 | 0 | 1 |

It was possible to observe the decrease of the educt (5'-O-protected nucleoside) and the increase of the product (5'-O-deprotected nucleoside) in the chromatograms obtained Evaluation was carried out over the area of the individual peaks. For reference purposes, the solution of the nucleoside to be irradiated was injected at zero minute (i.e. before irradiation) and the area of the peak obtained regarded as 100% educt. The procedure was the same for the product. The peak area of a 0.1 mmolar solution was determined and taken as 100%. The relevant areas of the products and educts at other times were based on these reference values.

From the curves thus obtained (conc. in % applied vis-á-vis the time), the following values were read.

$t_H$: half-change value=time when half of the educt had been reacted Conc. $t_{end}$: concentration of the product at the last point of examination Usually, this point was selected in such a manner that the educt was no longer detectable.

The results of the irradiation experiments are summarised in table 2.

As can be taken from table 2, there are but small variations of the half-change values of the different nucleosides. While the 5'-O-[2-(5-iodo-2-nitrophenyl)propoxy carbonyl derivative (compound 29) has the shortest half-change value at 23 seconds, this value is 44 seconds for 5'-O-[2-(2,5-dinitrophenyl)propoxy carbonyl thymidine (compound 37).

As far as the yield of the deprotected nucleosides is concerned, table 2 shows that the yield is highest at 97% for 5'-O-[2-(5-chloro-2-nitrophenyl)propoxycarbonyl]N$^6$-phenyloxyacetyl-2'-deoxyadenosine (compound 27), while it has values between approx. 75 and 95% for the other nucleoside derivatives.

TABLE 2

Results of the irradiation experiments

| Example | Compound | Half-change value $t_H$ | Conc. $t_{end}$ ($t_{end}$) |
|---|---|---|---|
| D1 | 5'-O-[2-(5-chloro-2-nitrophenyl)-propoxycarbonyl] thymidine (15) | 38 sec. | 91% (5 min) |
| D2 | 5'-O-[2-(5-bromo-2-nitrophenyl)-propoxy carbonyl] thymidine (19) | 32 sec. | 94% (5 min) |
| D3 | 5'-O-[2-(5-iodo-2-nitrophenyl)propoxy carbonyl] thymidine (23) | 25 sec. | 86% (5 min) |
| D4 | 5'-O-[2-(2,5-Dinitrophenyl)propoxy-carbonyl] thymidine (37) | 44 sec. | 75% (10 min) |
| D5 | 5'-O-[2-(5-chloro-2-nitrophenyl)-propoxycarbonyl]-N$^6$-phenyl-oxyacetyl-2'-deoxyadenosine (27) | 35 sec. | 97% (5 min) |
| D6 | 5'-O-[2-(5-bromo-2-nitrophenyl)-propoxycarbonyl]-N$^6$-phenyl-oxyacetyl-2'-deoxyadenosine (28) | 30 sec. | 95% (5 min) |
| D7 | 5'-O-[2-(5-iodo-2-nitrophenyl)propoxy-carbonyl]-N$^6$-phenyloxyacetyl-2'-desoxyadenosin (29) | 23 sec. | 95% (5 min) |

What is claimed is:
1. A compound of the general formula (I)

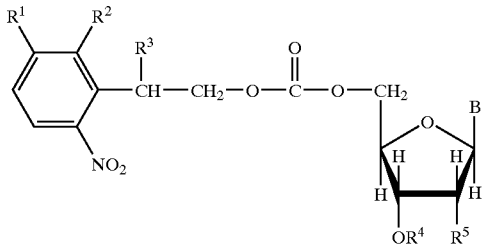

wherein
$R^1$=H, F, Cl, Br, I, or NO$_2$;
$R^2$=H or CN,
provided that $R^1$ and $R^2$ are not H at the same time;
$R^3$=H, an alkyl radical comprising 1 to 4 carbon atoms, or phenyl;
$R^4$=H or a phosphite amide group of the formula

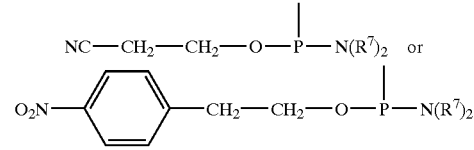

wherein the $R^7$ groups are the same or different and independently represent linear or branched alkyl radicals having 1 to 4 carbon atoms;
$R^5$=H, OH, halogen or XR$^6$, wherein X=O or S, and R$^6$ is a protective group; and
B=adenine, cytosine, guanine, thymine, uracil, 2,6-diaminopurine-9-yl, hypoxanthine-9-yl, 5-methylcytosine-1-yl, 5-amino-4-imidazolcarboxylic acid amide-1-yl or 5-amino-4-imidazol carboxylic acid amide-3-yl, with the proviso that when B=adenine, cytosine or guanine, the primary amino function optionally has a permanent protective group selected from the group consisting of phenoxy acetyl, 4-tert-butyl phenoxy acetyl, 4-isopropyl phenoxy acetyl, dimethyl formamidino, benzoyl, p-nitrophenyl ethoxy carbonyl (p-NPEOC), isobutyroyl, and p-nitrophenyl ethyl (p-NPE).

2. A compound according to claim 1 wherein $R^5$ is a group $XR^6$ and $R^6$ is an alkyl, alkenyl, acetal or silyl ether protective group when X=O or an alkyl protective group when X=S.

3. A compound according to claim 2 where an O-methyl or O-ethyl radical, an O-allyl radical, an O-tetrahydropyranyl or O-methoxytetrahydropyranyl radical or an O-t-butyldimethylsilyl radical is used as $R^5$.

4. A compound according to claim 1 wherein phenoxy acetyl, 4-tert-butyl phenoxy acetyl, 4-isopropyl phenoxy acetyl, dimethyl formamidino, benzoyl or p-nitrophenyl ethoxy carbonyl (p-NPEOC) radicals are used as the permanent protective group when B=adenine; phenoxy acetyl, 4-tert-butyl phenoxy acetyl, 4-isopropyl phenoxy acetyl, dimethyl formamidino, isobutyroyl, p-nitrophenyl ethyl (p-NPE) or p-NPEOC radicals are used as the permanent protective group when B=guanine; and phenoxy acetyl, 4-tert-butyl phenoxy acetyl, 4-isopropyl phenoxy acetyl, dimethyl formamidino, benzoyl, isobutyroyl or p-NPEOC radicals are used as permanent protective group when B=cytosine.

5. A process for preparing compounds according to claim 1 in at least two stages, comprising reacting a) an alcohol of the general formula (II)

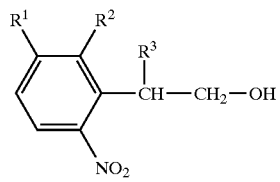

with a phosgene derivative selected from the group consisting of phosgene, chloroformic acid trichloromethyl ester, and bistrichloromethyl carbonate and then b) reacting the chlorocarbonic acid ester formed in stage a) with nucleosides the general formula (III)

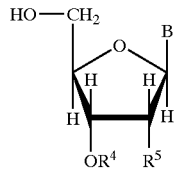

and, optionally, c) introducing the phosphite amide group

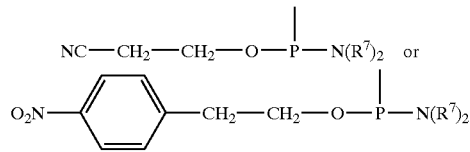

into position 3' of the nucleoside derivatives wherein $R^4$=H.

6. A process according to claim 5 wherein stage a) is conducted with a non-polar organic solvent selected from the group consisting of toluene and THF at temperatures between −20 and +25° C. and/or the phosgene derivative is used in a two- to five-fold excess based on the alcohol component.

7. A process according to claim 5 wherein stage b) is conducted in a solvent mixture consisting of dichloromethane and a polar organic solvent selected from the group consisting of DMF and pyridine at temperatures between −60 and +25° C.

8. A process according to claims 5 wherein a solvent mixture consisting of dichloromethane and DMF and a base selected from the group consisting of pyridine, triethyl amine and ethyl diisopropyl amine is used in stage b).

9. A process according to claim 5 wherein the mixing ratio of dichloromethane:pyridine or DMF, respectively, is 1:1 to 3:1 and/or the mol ratio of nucleoside:chlorocarbonic acid ester is 1:1 to 1:2.

10. A process according to claim 5, wherein the nucleoside dissolved in pyridine or DMF/base is fed in stage b) and a solution of the chlorocarbonic acid ester in dichloromethane is added dropwise.

11. A process according to claim 5 wherein the introduction of the phosphite amide group is effected by reacting the nucleoside derivatives with the corresponding phosphines in the presence of 1H tetrazol as activator in a solvent mixture consisting of dichloromethane and acetonitrile at temperatures between 0 and 25° C.

12. The process according to claim 6 wherein the non-polar organic solvent is toluene or THF.

13. The process according to claim 7 wherein the polar organic solvent is DMF or pyridine.

* * * * *